(12) United States Patent
Chen et al.

(10) Patent No.: US 9,240,555 B2
(45) Date of Patent: Jan. 19, 2016

(54) ORGANIC LUMINESCENT MATERIAL AND ORGANIC ELECTROLUMINESCENT APPARATUS

(71) Applicants: Au Optronics Corporation, Hsinchu (TW); Academia Sinica, Taipei (TW)

(72) Inventors: Chin-Ti Chen, Taipei (TW); Yi-Ting Lee, Taipei (TW); Meng-Ting Lee, Taipei (TW); Po-Hsuan Chiang, New Taipei (TW); Chieh-Wei Chen, Taichung (TW); Chung-Chun Lee, Hsinchu (TW)

(73) Assignees: Au Optronics Corporation, Hsinchu (TW); Academia Sinica, Taipei (TW)

( * ) Notice: Subject to any disclaimer, the term of this patent is extended or adjusted under 35 U.S.C. 154(b) by 568 days.

(21) Appl. No.: 13/677,317

(22) Filed: Nov. 15, 2012

(65) Prior Publication Data

US 2013/0126834 A1 May 23, 2013

(30) Foreign Application Priority Data

Nov. 17, 2011 (TW) .............................. 100142014 A

(51) Int. Cl.
| | |
|---|---|
| *H01L 51/54* | (2006.01) |
| *C09K 11/06* | (2006.01) |
| *H01L 51/00* | (2006.01) |
| *C07D 209/86* | (2006.01) |
| *C09B 57/00* | (2006.01) |
| *C09B 57/10* | (2006.01) |
| *C09B 69/00* | (2006.01) |
| *H01L 51/50* | (2006.01) |

(52) U.S. Cl.
CPC .......... *H01L 51/0061* (2013.01); *C07D 209/86* (2013.01); *C09B 57/00* (2013.01); *C09B 57/008* (2013.01); *C09B 57/10* (2013.01); *C09B 69/008* (2013.01); *C09K 11/06* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/185* (2013.01); *H01L 51/0067* (2013.01); *H01L 51/0068* (2013.01); *H01L 51/0072* (2013.01); *H01L 51/0081* (2013.01); *H01L 51/0085* (2013.01); *H01L 51/5016* (2013.01); *H01L 2251/308* (2013.01)

(58) Field of Classification Search
CPC ............ H01L 51/0059; H01L 51/0061; H01L 51/0067; H01L 51/0068; H01L 51/0072; H01L 51/50; H01L 51/5016; C09K 11/06; C09K 2211/1014; C09K 2211/1022; C09K 2211/185; C09B 57/00; C09B 57/008; C07D 209/86

See application file for complete search history.

(56) References Cited

U.S. PATENT DOCUMENTS

| | | |
|---|---|---|
| 2002/0117662 A1 | 8/2002 | Nii |
| 2008/0091021 A1 | 4/2008 | Kwok et al. |
| 2009/0045726 A1 | 2/2009 | Miki et al. |

FOREIGN PATENT DOCUMENTS

| | | |
|---|---|---|
| JP | 2005047811 | 2/2005 |
| TW | I280269 | 5/2007 |

OTHER PUBLICATIONS

English language machine translation of JP 2005/047811 A, 2005.*

*Primary Examiner* — Michael H Wilson
(74) *Attorney, Agent, or Firm* — Jianq Chyun IP Office

(57) ABSTRACT

An organic luminescent material includes a host luminescent material and a guest luminescent material. The host luminescent material includes a compound represented by formula (1), formula (1)

where n is 0~8; $R_2$ and $R_3$ respectively represent H, $CF_3$, CN, $CH_3$ or $C_5H_{11}$; $R_1$ is $CH_3$ or one of substituents shown as follows:

-continued
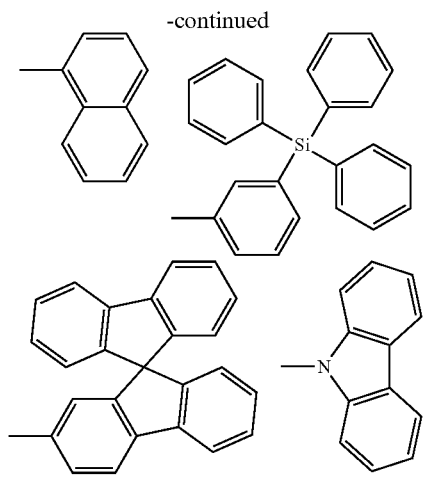
-continued
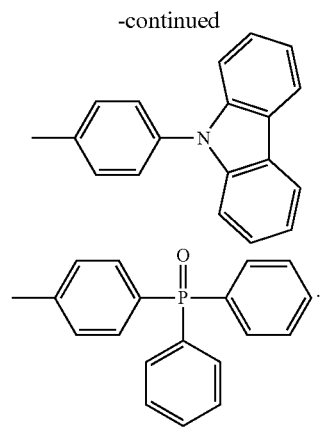
12 Claims, 1 Drawing Sheet

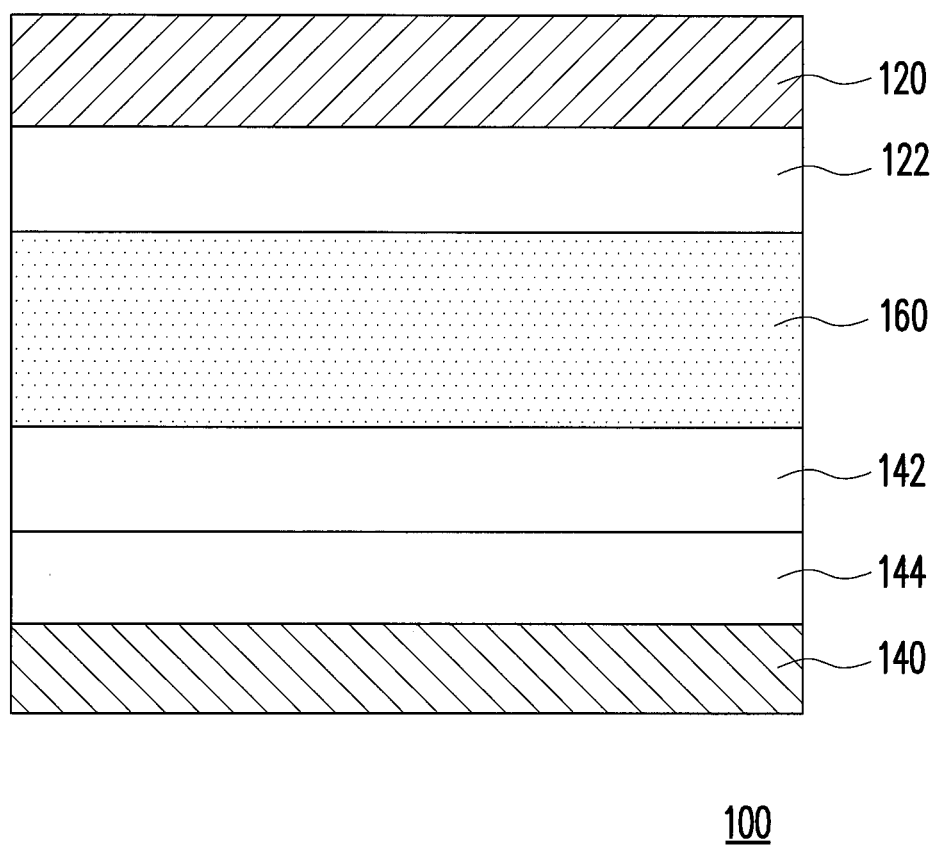

ORGANIC LUMINESCENT MATERIAL AND ORGANIC ELECTROLUMINESCENT APPARATUS

CROSS-REFERENCE TO RELATED APPLICATION

This application claims the priority benefit of Taiwan application serial no. 100142014, filed on Nov. 17, 2011. The entirety of the above-mentioned patent application is hereby incorporated by reference herein and made a part of this specification.

BACKGROUND OF THE INVENTION

1. Field of the Invention

The present invention relates to an organic electroluminescent apparatus, and more particularly to an organic luminescent material of the organic electroluminescent apparatus.

2. Description of Related Art

An electroluminescent device is a semiconductor device capable of converting electric energy into photonic energy with high conversion efficiency. Common applications of the electroluminescent device are an indicator light, a display panel, a luminescent device of an optical read/write head, and the like. The electroluminescent device has characteristics such as getting rid of a viewing angle problem, an easy process, low cost, a high response speed, a wide application temperature range and being full-color, therefore meeting requirements of display characteristics in a multimedia time and having a prospect of becoming a mainstream of a next-generation flat-panel display.

Generally, an organic electroluminescent apparatus includes an anode, an organic luminescent layer and a cathode. The organic luminescent layer includes a host luminescent material and a guest luminescent material. Holes and electrons in the organic electroluminescent device are mainly delivered into the host luminescent material for recombination, thereby producing energy, and the energy is transferred into the guest luminescent material to produce light. Therefore, the host luminescent material needs to have a desirable electron and hole transport property, and a triplet energy level of the host luminescent material should be greater than or equal to that of the guest luminescent material, to avoid energy loss caused by energy return.

Therefore, if the triplet energy level of the host luminescent material needs to be improved, a length of a conjugated chain in a molecule of the host luminescent material should be shortened. However, if the length of the conjugated chain in the molecule of the host luminescent material is shortened, a molecular weight of the molecule is reduced, and the reduced molecular weight of the host luminescent material decreases thermal stability (a glass transition temperature is used as a pointer in the following) of the host luminescent material.

SUMMARY OF THE INVENTION

Accordingly, the present invention provides an organic luminescent material having a high triplet energy level and desirable thermal stability.

The present invention provides an organic electroluminescent apparatus with the organic luminescent material, thereby having desirable external quantum efficiency (EQE).

The present invention provides an organic luminescent material, including a host luminescent material and a guest luminescent material. The host luminescent material may be a compound represented by formula (1),

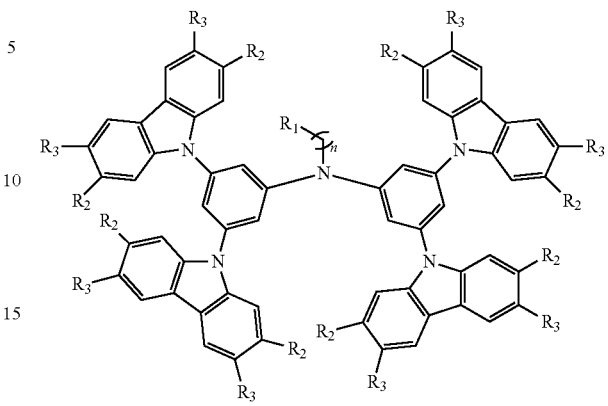

formula (1)

where n is 0~8; $R_2$ and $R_3$ respectively represent H, $CF_3$, CN, $CH_3$ or $C_5H_{11}$; $R_1$ is $CH_3$ or one of substituents shown as follows:

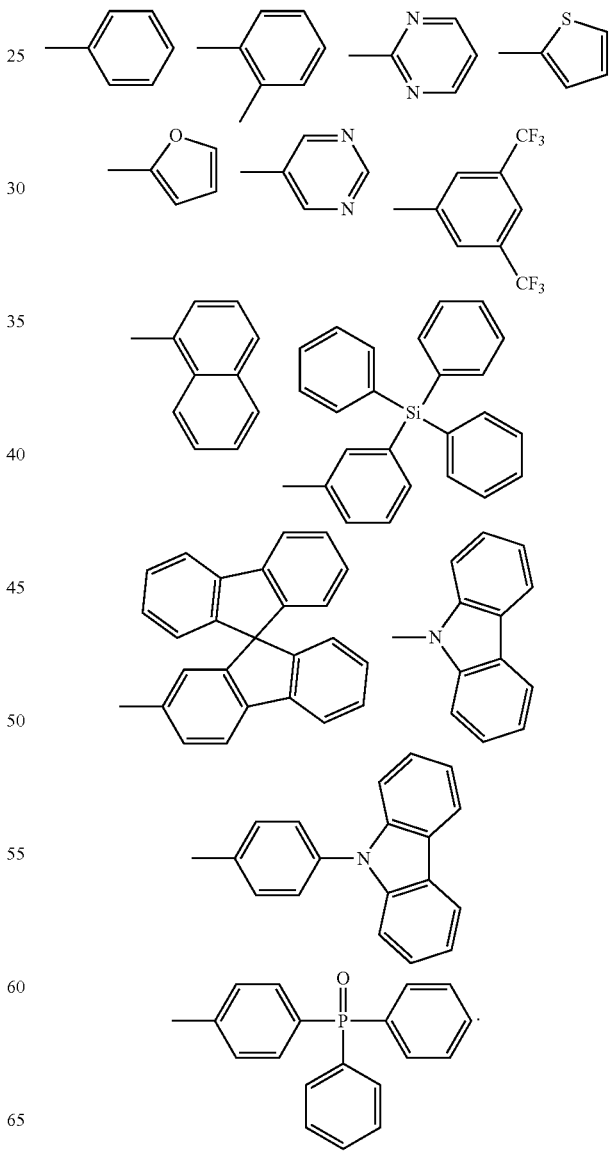

The present invention further provides an organic electroluminescent apparatus, including a first electrode layer, a second electrode layer and an organic luminescent layer. The organic luminescent layer is located between the first electrode layer and the second electrode layer. The organic luminescent layer includes a host luminescent material and a guest luminescent material. The host luminescent material includes a compound represented by formula (1), formula (1)

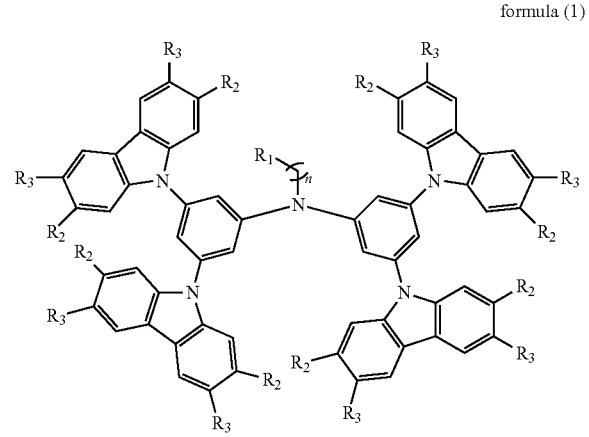

where n is 0~8; $R_2$ and $R_3$ respectively represent H, $CF_3$, CN, $CH_3$ or $C_5H_{11}$; $R_1$ is $CH_3$ or one of substituents shown as follows:

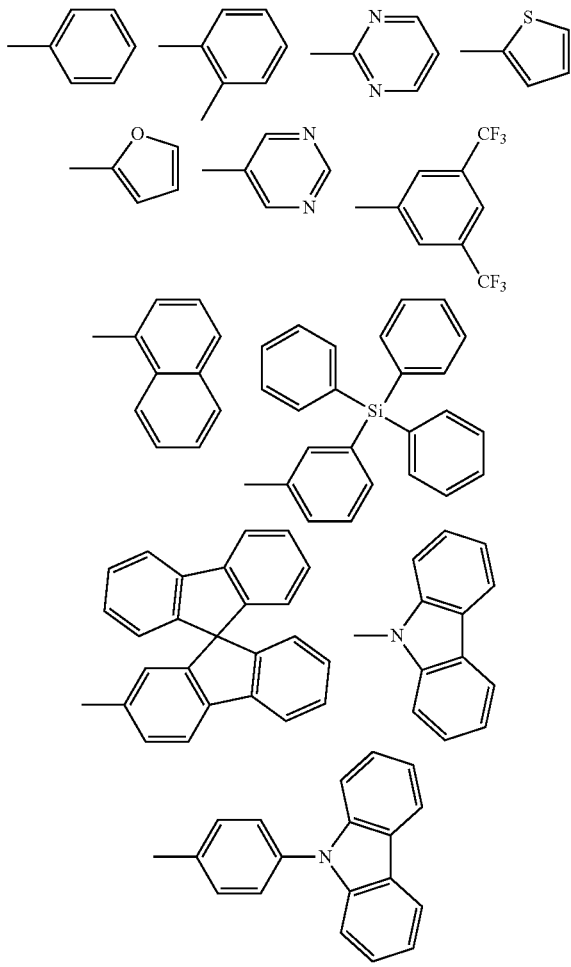

-continued

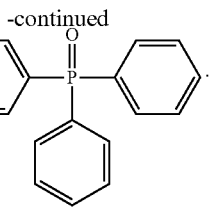

Based on the above, the host luminescent material of the organic luminescent material according to the present invention has a short conjugated chain, thereby having a high triplet energy level. Therefore, energy on the guest luminescent material is not easy to be returned to the host luminescent material, to reduce energy loss. In addition, the host luminescent material of the organic luminescent material according to the present invention has a characteristic of a high molecular weight, so that the organic luminescent material of the present invention has desirable thermal stability.

In order to make the aforementioned features and advantages of the present invention comprehensible, embodiments are described in detail below with reference to the accompanying drawings.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 1 is a schematic sectional view of an organic electroluminescent apparatus according to an embodiment of the present invention.

DESCRIPTION OF THE EMBODIMENTS

Reference will now be made in detail to the present embodiments of the invention, examples of which are illustrated in the accompanying drawings. Wherever possible, the same reference numbers are used in the drawings and the description to refer to the same or like parts.

Organic Luminescent Material

An organic luminescent material according to an embodiment of the present invention includes a host luminescent material and a guest luminescent material. The host luminescent material includes a compound represented by formula (1), formula (1)

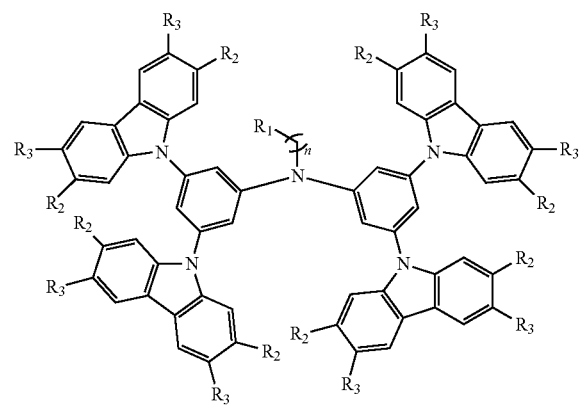

where n is 0~8; $R_2$ and $R_3$ respectively represent H, $CF_3$, CN, $CH_3$ or $C_5H_{11}$; $R_1$ is $CH_3$ or one of substituents shown as follows:

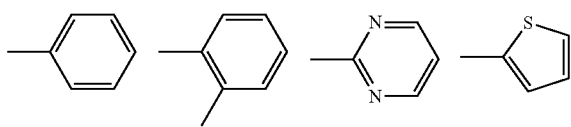

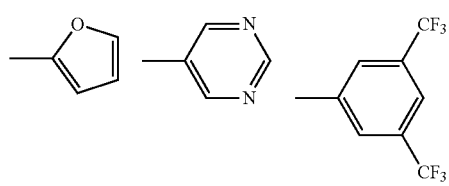

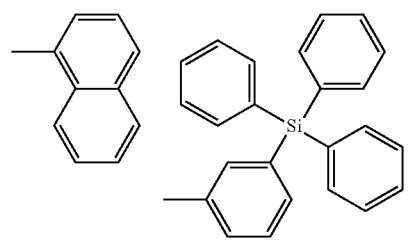

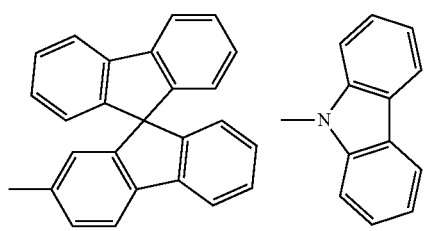

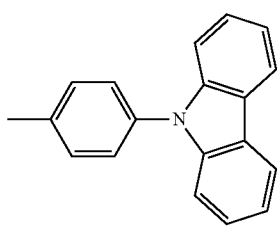

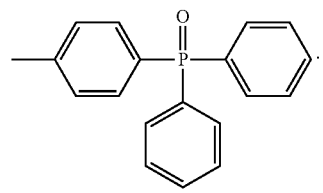

According to this embodiment, the host luminescent material may be, for example, one of the following compounds, where characters below each host luminescent material (for example N2PH, MPH, CF3, TH, CH3 and CH2PH) represent an abbreviation of the host luminescent material.

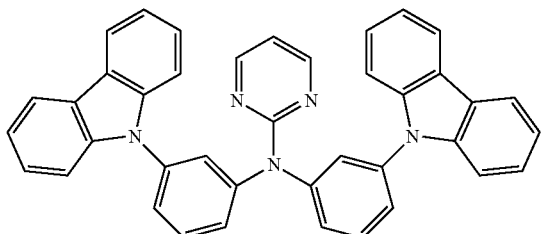

N2PH

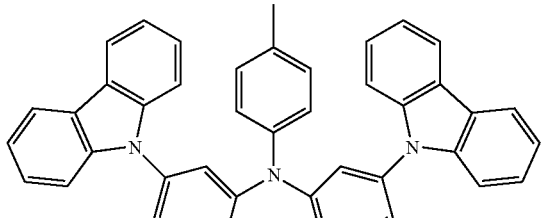

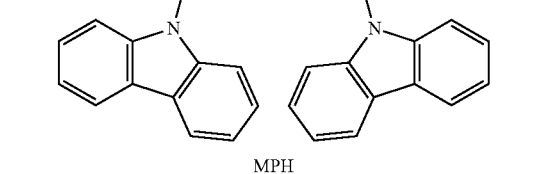

MPH

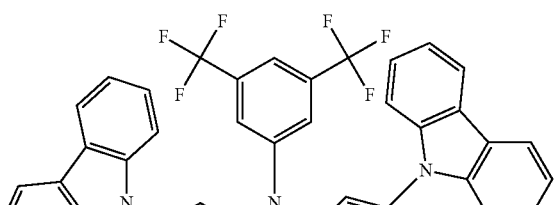

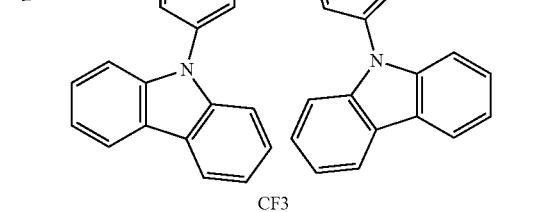

CF3

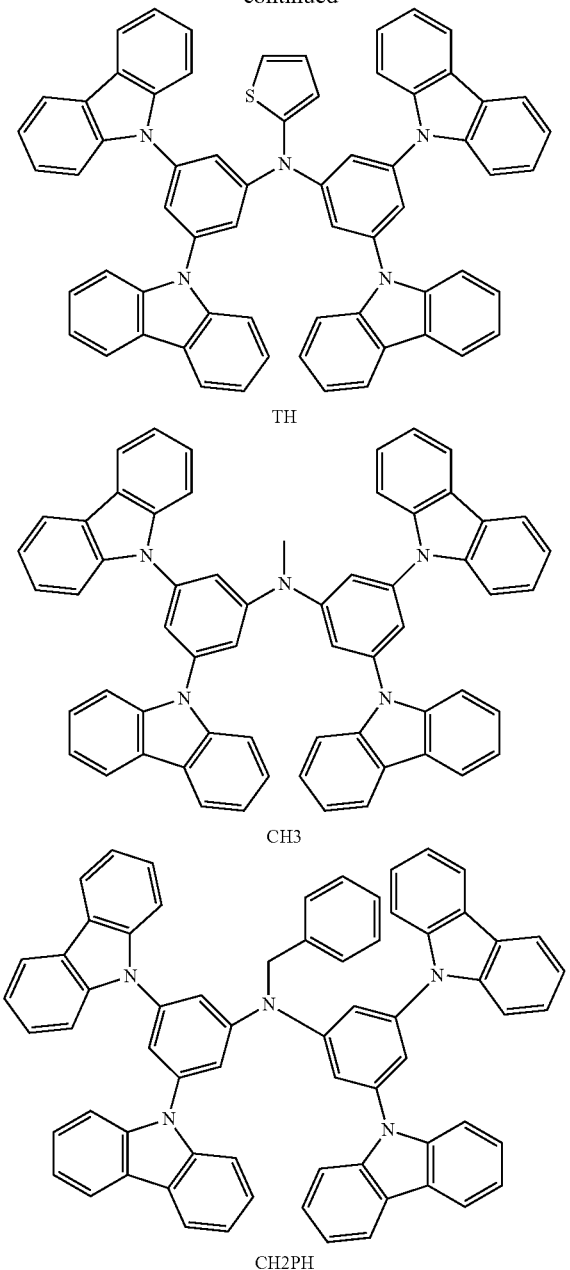

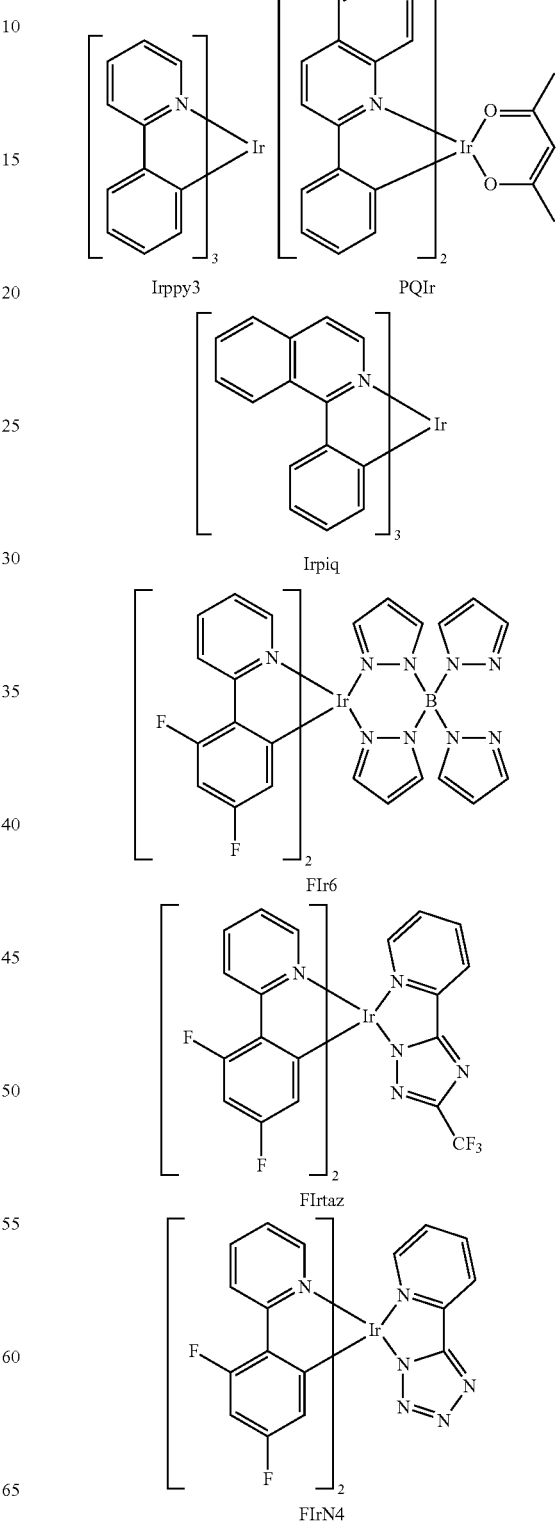

In addition, the guest luminescent material may be, for example, one of the following compounds, where characters below each guest luminescent material (for example Irppy3, PQIr, Irpiq, FIr6, FIrtaz, FIrN4 and FIrpic) represent an abbreviation of the guest luminescent material.

In this embodiment, the host luminescent material accounts for, for example, 80% to 95% by weight of an organic luminescent layer. The guest luminescent material accounts for, for example, 5% to 20% by weight of the organic luminescent layer.

According to this embodiment, a glass transition temperature (Tg) of the host luminescent material is substantially greater than 80 degrees Celsius, making desirable thermal stability. Generally, an exothermic phenomenon occurs when the organic electroluminescent apparatus emits light, and therefore the luminescent material used by the organic electroluminescent apparatus needs to have appropriate thermal stability. Usually, the glass transition temperature (Tg) above 80 degrees Celsius is an index for evaluating whether the luminescent material is applicable or not. Therefore, the host luminescent material of this embodiment is applicable to the organic electroluminescent apparatus.

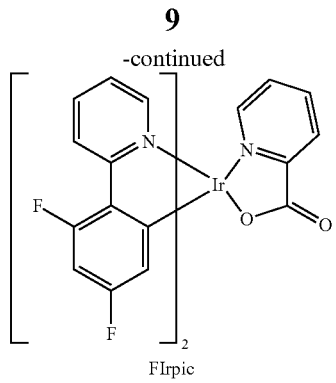

FIrpic

Generally, if luminescent efficiency of the organic luminescent layer needs to be improved, the triplet energy level of the host luminescent material should be higher than or equal to that of the guest luminescent material.

Host Luminescent Material and Synthesis Method Thereof

In order to describe the host luminescent material of the present invention, processes of several synthesis embodiments are listed below. First of all, before an end product of the host luminescent material is made, an initial product bis(3,5-di(9H-carbazol-9-yl)phenyl)amine (CzPA) is synthesized. Afterwards, the host luminescent material is synthesized with the head product CzPA.

Initial Product CzPA

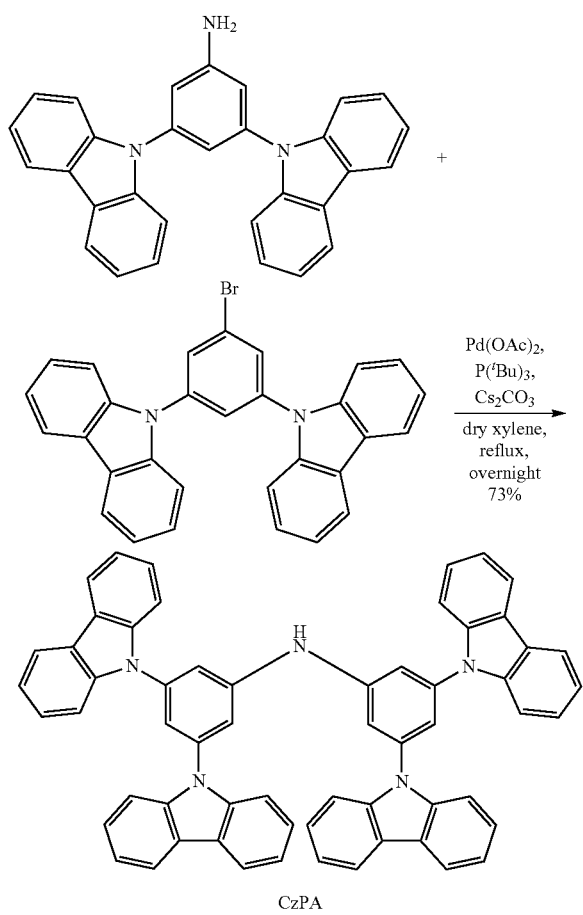

CzPA

A 100 ml two-neck flask was taken and added with a magnet, and a return pipe was set up. Water was removed by baking the flask under vacuum. Then 3,5-Di(9H-carbazol-9-yl)aniline (3.0 g, 7.1 mmol), 9,9'-(5-bromo-1,3-phenylene)bis(9H-carbazole) (3.5 g, 7.2 mmol), $Cs_2CO_3$ (2.54 g, 7.8 mmol), $Pd(OAc)_2$ (0.04 g, 0.18 mmol) and dry xylene (40 ml) were added under nitrogen. Finally, tri-tert-butyl Phosphine (0.14 g, 0.69 mmol) was dropped, and the flask was put into a preheated oil bath pan at 120° C. and refluxed for 20 hours. The temperature was cooled down to the room temperature, and products after reaction were extracted by a large amount of dichloromethane. The organic layer was collected, and water was removed by anhydrous magnesium sulfate. Then, the desiccant was removed through filtering. The filtrate was concentrated by spinning, so that the solvent was drained. The solid was separated and purified through the silica gel column chromatography, and was flushed by a mixture solution of dichloromethane/normal hexane (2:3) to obtain the white product. The yield is 73%.

Synthesis Embodiment 1

N,N-bis(3,5-di(9H-carbazol-9-yl)phenyl)pyrimidin-2-amine, abbreviated to N2PH

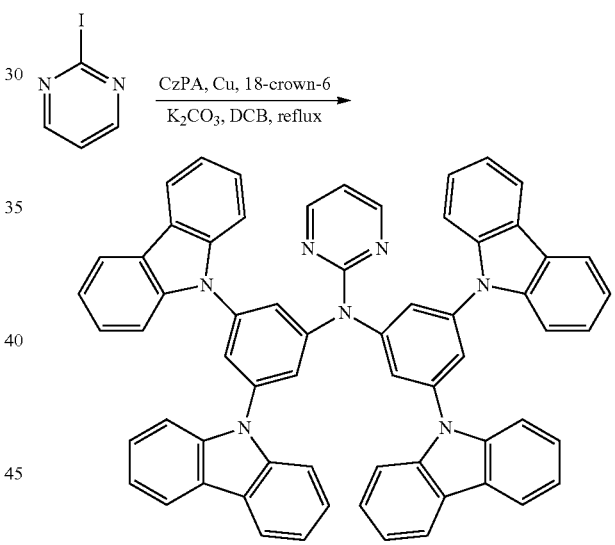

A 10 ml two-neck flask was taken and added with a magnet, and a return pipe was set up. Water was removed by baking the flask under vacuum. Then, 2-iodopyrimidine (0.06 g, 0.29 mmol), CzPA (0.2 g, 0.24 mmol), potassium carbonate (0.04 g, 0.29 mmol), copper powder (0.018 g, 0.28 mmol), 18-crown-6 (0.013 g, 0.05 mmol) and dichlorobenzene (5 ml) were added under nitrogen. The reactants were put into a preheated oil bath pan at 180° C. and the reaction lasted for 24 hours. The temperature was cooled down to the room temperature, and dichlorobenzene was first removed by a vacuum distillation unit. Afterwards, the products were extracted by dichloromethane and water, the organic layer was collected, and water was removed by anhydrous magnesium sulfate. Then, the desiccant was removed through filtering. The filtrate was concentrated by spinning, so that the solvent was drained. The solid was separated and purified through the silica gel column chromatography, and was flushed by dichloromethane/hexane (1:4) to obtain the white product.

Synthesis Embodiment 2

N,N-bis(3,5-di(9H-carbazol-9-yl)phenyl)thiophen-2-amine, abbreviated to TH

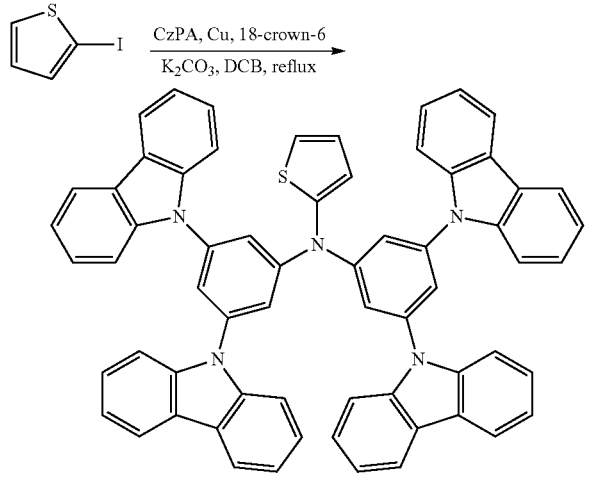

A 10 ml two-neck flask was taken and added with a magnet, and a return pipe was set up. Water was removed by baking the flask under vacuum. Then, 2-iodothiophene (0.04 g, 0.18 mmol), CzPA (0.1 g, 0.12 mmol), potassium carbonate (0.02 g, 0.15 mmol), copper powder (0.009 g, 0.14 mmol), 18-crown-6 (0.006 g, 0.03 mmol) and dichlorobenzene (5 ml) were added under nitrogen. The reactants were put into a preheated oil bath pan at 180° C. and the reaction lasted for 24 hours. The temperature was cooled down to the room temperature, and dichlorobenzene was removed by a vacuum distillation unit. Afterwards, the products were extracted by dichloromethane and water, the organic layer was collected, and water was removed by anhydrous magnesium sulfate. Then, the desiccant was removed through filtering. The filtrate was concentrated by spinning, so that the solvent was drained. The solid was separated and purified through the silica gel column chromatography, and was flushed by dichloromethane/hexane (1:4) to obtain the white product.

Synthesis Embodiment 3

3,5-di(9H-carbazol-9-yl)-N-(3,5-di(9H-carbazol-9-yl)phenyl)-N-methylaniline, abbreviated to CH3

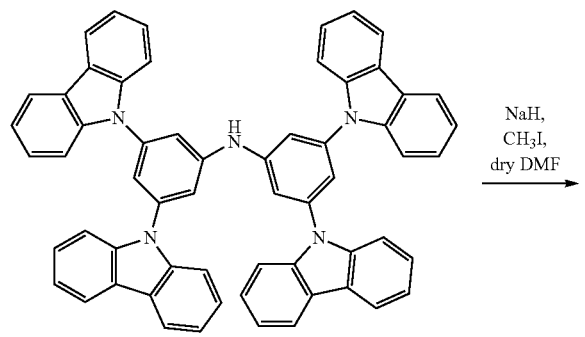

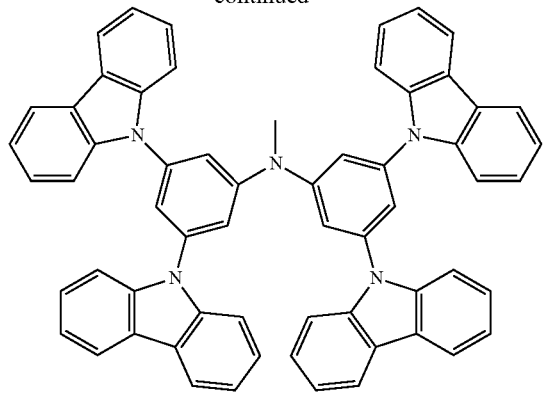

A 10 ml two-neck flask was taken and added with a magnet, and a return pipe was set up. Water was removed by baking the flask under vacuum. Then, CzPA (0.1 g, 0.12 mmol) and dried N,N-dimethyl formamide (DMF) (5 ml) were added under nitrogen and fully dissolved. Sodium hydride (0.005 g, 60%, 0.13 mmol) was added, and the obtained mixture was stirred for ten minutes at the room temperature. Finally, iodomethane (0.02 g, 0.16 mmol) was added and the obtained mixture was reacted at 60° C. for 2 hours. The reactants were poured into water with ice to terminate the reaction. The solid was filtered. The obtained solid is flushed by solution of dichloromethane/normal hexane (1:5), and was treated with column chromatography to purify the product. The yield is about 88%.

Synthesis Embodiment 4

N-benzyl-3,5-di(9H-carbazol-9-yl)-N-(3,5-di(9H-carbazol-9-yl)phenyl)aniline, abbreviated to CH2PH

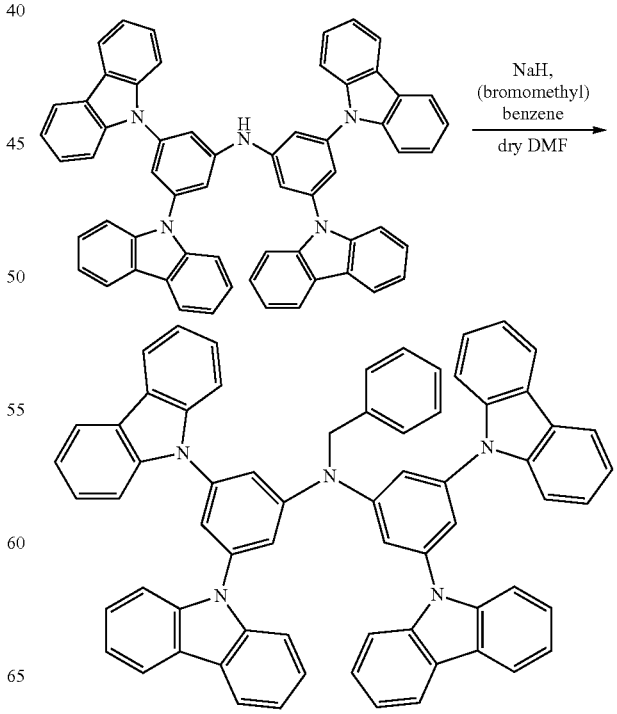

A 10 ml two-neck flask was taken and added with a magnet, and a return pipe was set up. Water was removed by baking the flask under vacuum. Then, CzPA (0.1 g, 0.12 mmol) and dry DMF (5 ml) were added under nitrogen, and were fully dissolved. Sodium hydride (0.005 g, 60%, 0.13 mmol) was added, and the obtained mixture was stirred for ten minutes at the room temperature. Finally, (bromomethyl)benzene (0.03 g, 0.16 mmol) was added and the obtained mixture was reacted at 60° C. for 2 hours. Water was added to terminate the reaction. The products were extracted by dichloromethane, water of the organic layer was removed by magnesium sulfate, and the organic layer was drained. The obtained solid was flushed with a solution of dichloromethane/normal hexane (1:5), and was treated with column chromatography to purify the product. The yield is about 85%.

Synthesis Embodiment 5

3,5-di(9H-carbazol-9-yl)-N-(3,5-di(9H-carbazol-9-yl)phenyl)-N-p-tolylaniline, abbreviated to MPH

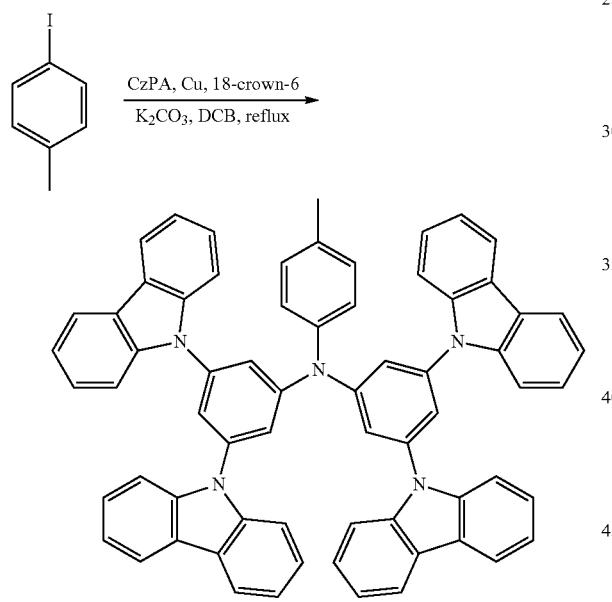

A 10 ml two-neck flask was taken and added with a magnet, and a return pipe was set up. Water was removed by baking the flask under vacuum. Then, 1-iodo-4-methylbenzene (0.03 g, 0.14 mmol), CzPA (0.1 g, 0.12 mmol), potassium carbonate (0.02 g, 0.14 mmol), copper powder (0.009 g, 0.14 mmol), 18-crown-6 (0.006 g, 0.02 mmol), dichlorobenzene (5 ml) were added under nitrogen. The reactants were put into a preheated oil bath pan at 180° C. and the reaction lasted for 24 hours. The temperature was cooled down to the room temperature, and the dichlorobenzene was removed by a vacuum distillation unit. Afterwards, the products were extracted by dichloromethane and water, the organic layer was collected, and water was removed by anhydrous magnesium sulfate. The desiccant was removed through filtering. The filtrate was concentrated by spinning, so that the solvent was drained. The solid was separated and purified through the silica gel column chromatography, and was flushed by dichloromethane/hexane (1:4) to obtain the white product.

Synthesis Embodiment 6

N-(3,5-bis(trifluoromethyl)phenyl)-3,5-di(9H-carbazol-9-yl)-N-(3,5-di(9H-carbazol-9-yl)phenyl)aniline, abbreviated to CF3

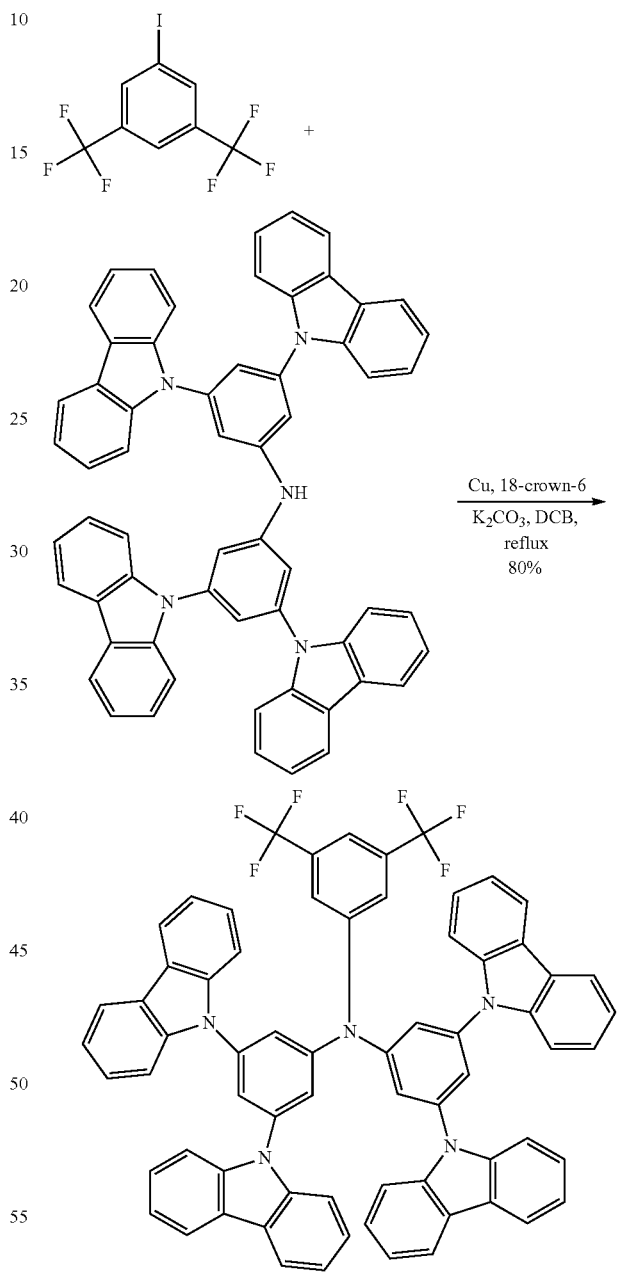

A 10 ml two-neck flask was taken and added with a magnet, and a return pipe was set up. Water was removed by baking the flask under vacuum. Then, 1-iodo-3,5-bis(trifluoromethyl)benzene (0.05 g, 0.14 mmol), CzPA (0.1 g, 0.12 mmol), potassium carbonate (0.02 g, 0.14 mmol), copper powder (0.009 g, 0.14 mmol), 18-crown-6 (0.006 g, 0.02 mmol) and dichlorobenzene (5 ml) were added under nitrogen. The reactants were put into a preheated oil bath pan at 180° C. and the reaction lasted for 24 hours. The temperature was cooled down to the room temperature, and dichlorobenzene was removed by a vacuum distillation unit. Afterwards, the products were extracted by dichloromethane and water, the organic layer was collected, and water was removed by anhydrous magnesium sulfate. The desiccant was removed through filtering. The filtrate was concentrated by spinning, so that the solvent was drained. The solid was separated and purified through the silica gel column chromatography, and was flushed by dichloromethane/hexane (1:4) to obtain the flavescent product. The yield is 80%.

Method for Evaluating the Host Luminescent Material

The manner for evaluating the above host luminescent materials is to test the triplet energy level and the glass transition temperature of the compounds of synthesis embodiments 1 to 6. In addition, conventional host luminescent materials 4,4'-N,N'-dicarbazole-biphenyl (CBP) and N,N'-dicarbazolyl-3,5-benzene (mCP) are used as comparative embodiment 1 and comparative embodiment 2, and the triplet energy levels and the glass transition temperatures thereof are tested respectively. Table 1 shows the triplet energy levels and the glass transition temperatures of synthesis embodiments 1 to 6 and comparative embodiments 1 to 2.

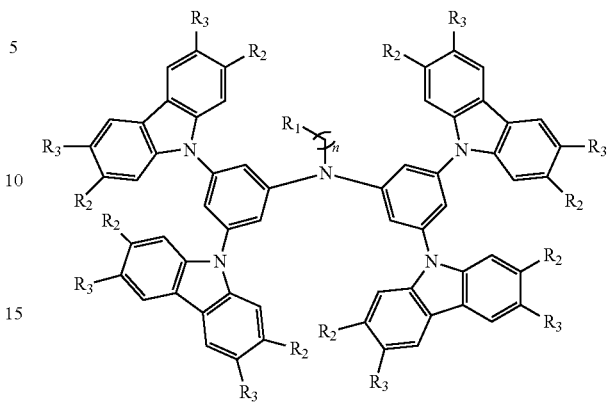

formula (1)

where n is 0~8; $R_2$ and $R_3$ respectively represent H, $CF_3$, CN, $CH_3$ or $C_5H_{11}$; $R_1$ is $CH_3$ or one of substituents shown as follows:

TABLE 1

| | Comparative embodiment 1 | Comparative embodiment 2 | Synthesis embodiment 1 | Synthesis embodiment 2 | Synthesis embodiment 3 | Synthesis embodiment 4 | Synthesis embodiment 5 | Synthesis embodiment 6 |
|---|---|---|---|---|---|---|---|---|
| Triplet energy level (eV) | 2.6 | 2.9 | 2.78 | 2.8 | 2.93 | 2.9 | 2.9 | 2.76 |
| Glass transition temperature (° C.) | — | 65 | 175 | 168 | 155 | 158 | 170 | 175 |

It can be known from Table 1 that, the triplet energy levels of synthesis embodiments 1 to 6 are higher than that of comparative embodiment 1. FIrpic is taken as an example of the guest luminescent material. The triplet energy levels of synthesis embodiments 1 to 6 are higher than that of the guest luminescent material FIrpic (2.7 eV). In addition, although the triplet energy level of comparative embodiment 2 is higher than that of the FIrpic, the glass transition temperature of comparative embodiment 2 is only 65° C. The glass transition temperature of synthesis embodiments 1 to 6 are all greater than that of the mCP, and are greater than 80° C. Therefore, synthesis embodiments 1 to 6 have desirable thermal stability, and are suitable to be used as the host luminescent material in the organic luminescent layer.

Organic Electroluminescent Apparatus

The present invention further provides an organic electroluminescent apparatus 100. FIG. 1 is a schematic sectional view of an organic electroluminescent apparatus 100 according to an embodiment of the present invention. Referring to FIG. 1, the organic electroluminescent apparatus 100 includes a first electrode layer 120, a second electrode layer 140 and an organic luminescent layer 160. The organic luminescent layer 160 is located between the first electrode layer 120 and the second electrode layer 140.

The organic luminescent layer 160 includes a host luminescent material and a guest luminescent material. The host luminescent material may be a compound represented by formula (1),

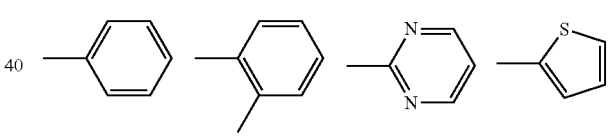

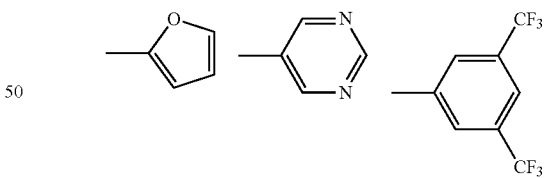

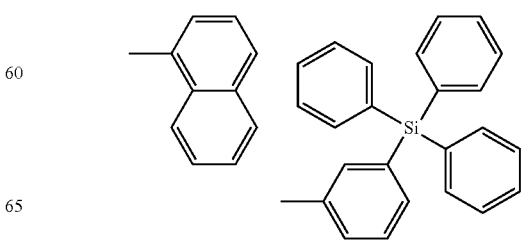

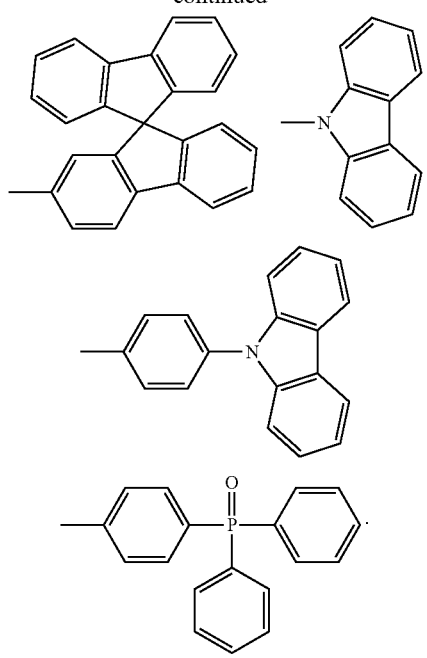
According to this embodiment, the host luminescent material may be, for example, one of the following compounds:
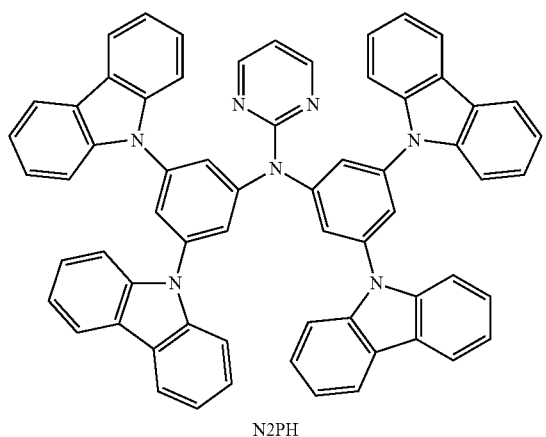
N2PH
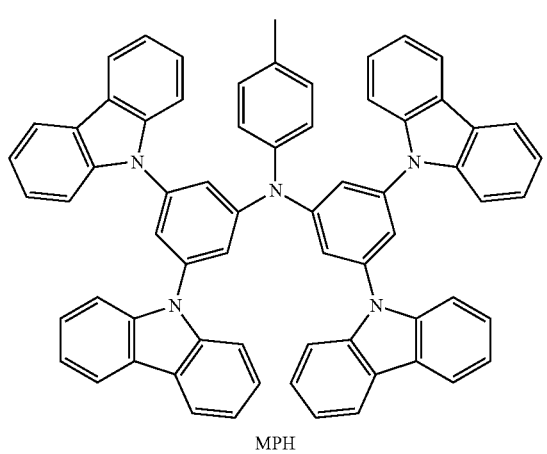
MPH
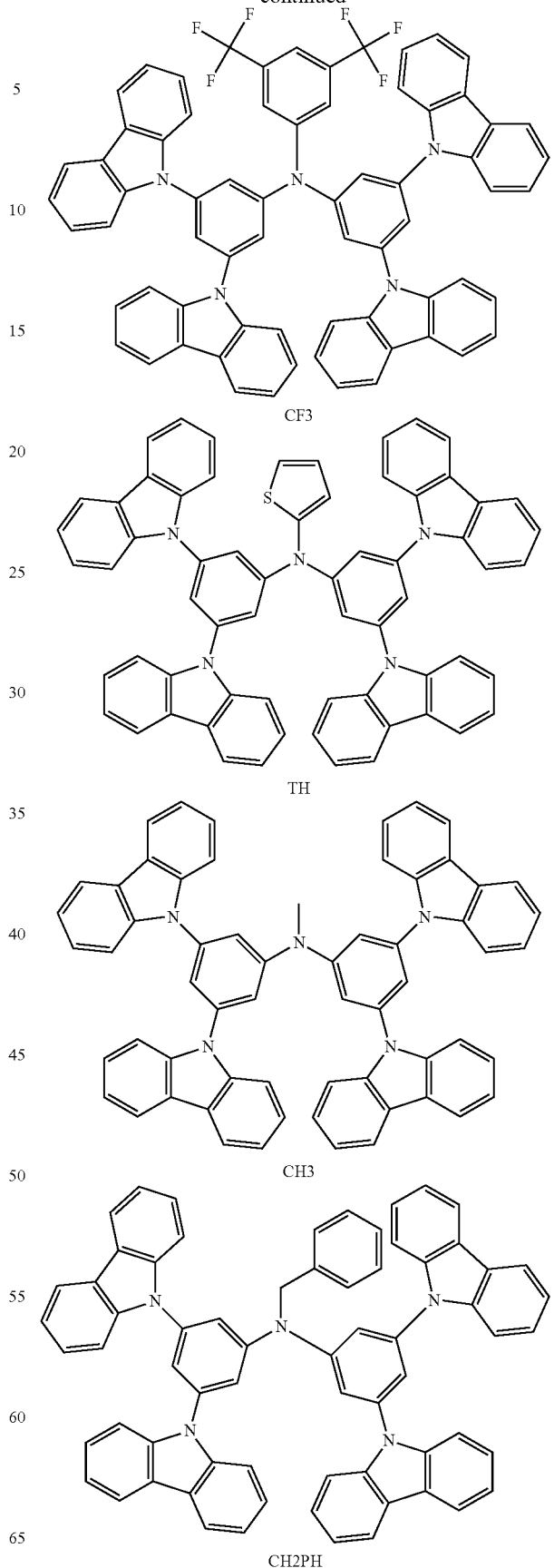
CF3
TH
CH3
CH2PH In addition, according to this embodiment, the host luminescent material accounts for, for example, 80% to 95% by weight of the organic luminescent layer 160. A glass transition temperature (Tg) of the host luminescent material is substantially greater than 80 degrees Celsius.

In addition, according to this embodiment, the guest luminescent material accounts for, for example, 5% to 20% by weight of the organic luminescent layer 160. The guest luminescent material may be, for example, one of the following compounds:

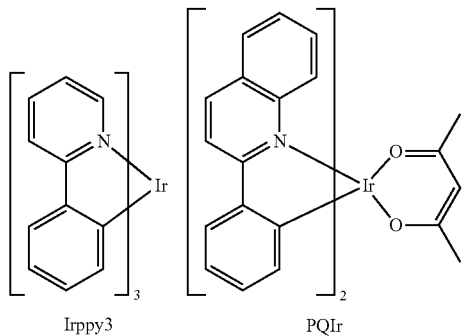

Irppy3    PQIr

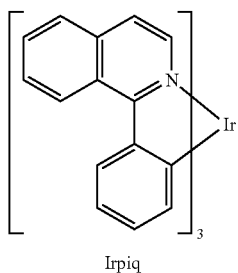

Irpiq

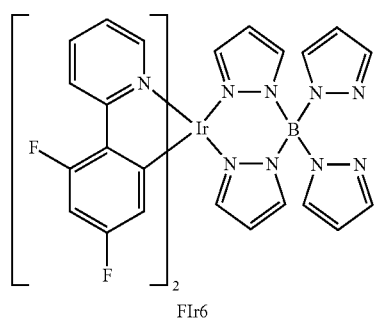

FIr6

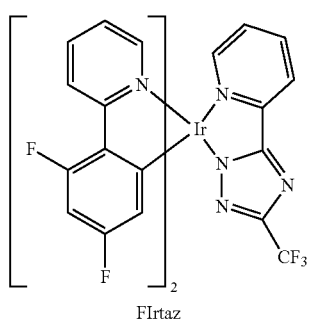

FIrtaz

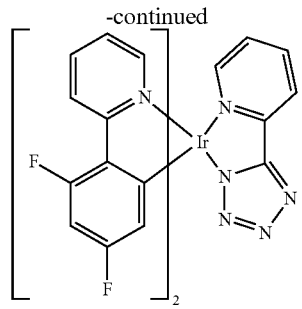

FIrN4

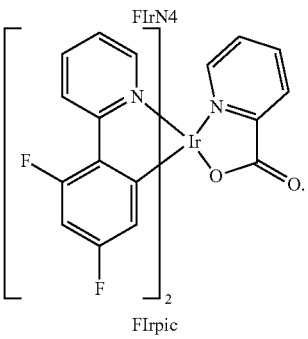

FIrpic

According to this embodiment, the second electrode layer 140 is of a transparent electrode material, and may be, for example, indium tin oxide (ITO). A material of the first electrode layer 120 may be, for example, metal, a transparent conducting material or other appropriate conducting materials. However, the present invention is not limited thereto. In another embodiment, the second electrode layer 140 may be, for example, metal, a transparent conducting material or other appropriate conducting materials, while the first electrode layer 120 may be, for example, a transparent electrode material. Specifically, at least one of the first electrode layer 120 and the second electrode layer 140 of this embodiment is of the transparent electrode material. In this manner, light emitted by the organic luminescent layer 160 may go out through the transparent electrode, so that the organic electroluminescent apparatus 100 emits light.

In addition, the organic electroluminescent apparatus 100 of this embodiment further includes an electron transport layer 122, a hole transport layer 142 and a hole injection layer 144. The electron transport layer 122 is located between the organic luminescent layer 160 and the first electrode layer 120. The hole transport layer 142 is located between the organic luminescent layer 160 and the second electrode layer 140. The hole injection layer 144 is located between the hole transport layer 142 and the second electrode layer 140.

A material of the electron transport layer 122 may be, for example, aluminum bis(2-methyl-8-quinolinato)4-phenylphenolate (Balq). The electron transport layer 122 may facilitate the delivery of electrons from the electrode to the organic luminescent layer 160. A material of the hole transport layer 142 may be, for example, N,N'-bis(1-naphthyl)-N,N'-diphenyl-1,1'-biphenyl-4,4'diamine (NPB). A material of the hole injection layer 144 may be, for example, copper phthalocyanine (CuPC). The hole transport layer 142 and the hole injection layer 144 may reduce the energy barrier for injecting holes from the electrode into the organic luminescent layer and meanwhile reduce a driving voltage.

EXAMPLES

Specifically, the material of the first electrode layer of the organic electroluminescent apparatus is aluminum, and a thickness thereof is 150 nanometers. The material of the electron transport layer is Balq, and a thickness thereof is 40 nanometers. The material of the second electrode layer is ITO. The material of the hole transport layer is NPB, and a thickness thereof is 30 nanometers. The material of the hole injection layer is CuPC, and a thickness thereof is 10 nanometers. A thickness of the organic luminescent layer is 30 nanometers. FIrpic is used as the guest luminescent material of the organic luminescent layer, synthesis embodiment 3 (CH3) is used as the host luminescent material of examples 1 to 3, and comparative embodiment 2 (mCP) is used as the host luminescent material of comparison example 1. The above film layers are applied to the organic electroluminescent apparatus, and the organic electroluminescent apparatus is evaluated. In addition, the guest luminescent material FIrpic of different concentrations is doped in examples 1 to 3, to further disclose influence of the doping concentration on the organic electroluminescent apparatus. Table 2 shows the guest luminescent material doping concentrations and the EQE of the organic electroluminescent apparatuses of comparison example 1 and examples 1 to 3.

TABLE 2

|  | FIrpic doping concentration (%) | EQE (%) |
| --- | --- | --- |
| Comparison example 1 | 6 | 7.8 |
| Example 1 | 10 | 11.9 |
| Example 2 | 15 | 12.2 |
| Example 3 | 20 | 10.6 |

It can be known from Table 2 that, the EQE of examples 1 to 3 is higher than that of comparison example 1, indicating conversion efficiency from electron to photon of the organic electroluminescent apparatuses of examples 1 to 3 is better than that of the organic electroluminescent apparatus of comparison example 1. In addition, the organic electroluminescent apparatuses of examples 1 to 3 have different FIrpic doping concentrations. It can be known from Table 2 that, as the FIrpic doping concentration rises from 10% to 15%, the EQE of the organic electroluminescent apparatus rises from 11.9% to 12.2%. However, when the FIrpic doping concentration is 20%, the EQE of the organic electroluminescent apparatus is 10.6%. Such a result indicates that the EQE of the organic luminescent apparatus rises as the FIrpic doping concentration increases. However, when the FIrpic doping concentration is 15% (that is, saturation concentration), the EQE of the organic electroluminescent apparatus stops rising.

In conclusion, the host luminescent material of the present invention has a short conjugated chain, therefore having a triplet energy level higher than that of the guest luminescent material. In this manner, exciton on the guest luminescent material is not easy to be returned to the host luminescent material, preventing energy loss. In addition, the host luminescent material of the organic luminescent material of the present invention has high molecular weight, therefore having a high glass transition temperature. In this manner, the host luminescent material has desirable thermal stability, and is applicable to the organic electroluminescent apparatus. The organic electroluminescent apparatus of the present invention adopts the above host luminescent material, therefore having describable EQE; the organic electroluminescent apparatus may have desirable thermal stability when operating.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An organic luminescent material, comprising a host luminescent material and a guest luminescent material, wherein the host luminescent material comprises a compound represented by formula (1),

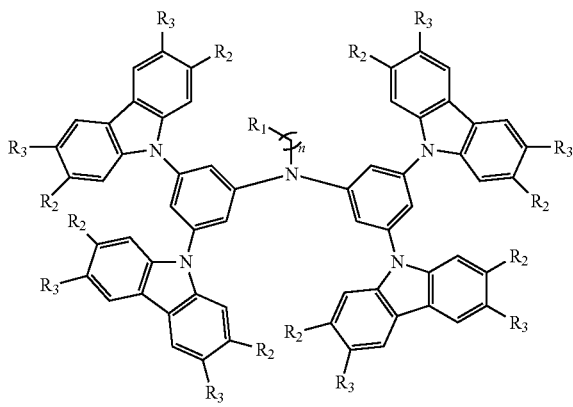

formula (1)

wherein n is 0~8;

$R_2$ and $R_3$ respectively represent H, $CF_3$, CN, $CH_3$ or $C_5H_{11}$; and $R_1$ is one of substituents shown as follows:

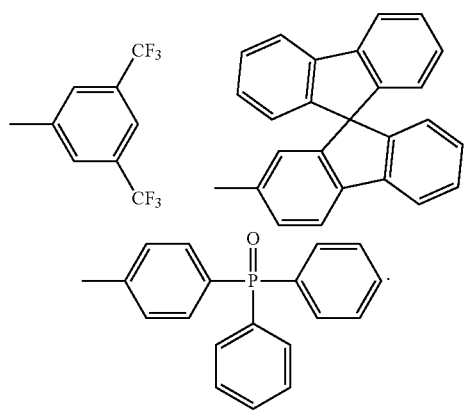

2. The organic luminescent material according to claim 1, wherein the host luminescent material comprises the following compound:

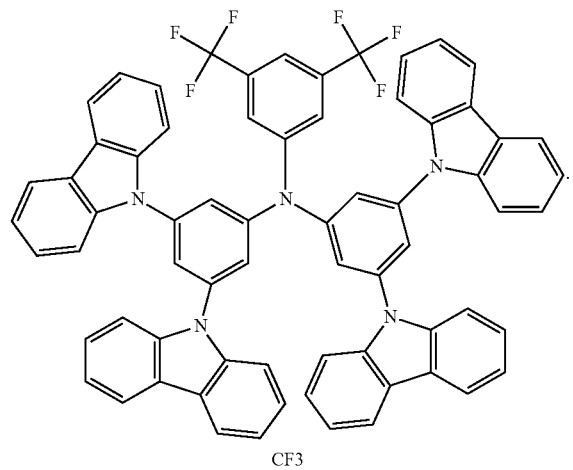

3. The organic luminescent material according to claim 1, wherein a glass transition temperature (Tg) of the host luminescent material is greater than 80 degrees Celsius.

4. The organic luminescent material according to claim 1, wherein the host luminescent material accounts for 80% to 95% by weight of the organic luminescent material.

5. An organic electroluminescent apparatus, comprising:

a first electrode layer;

a second electrode layer; and an organic luminescent layer, located between the first electrode layer and the second electrode layer, wherein the organic luminescent layer comprises a host luminescent material and a guest luminescent material, and the host luminescent material comprises a compound represented by formula (1):

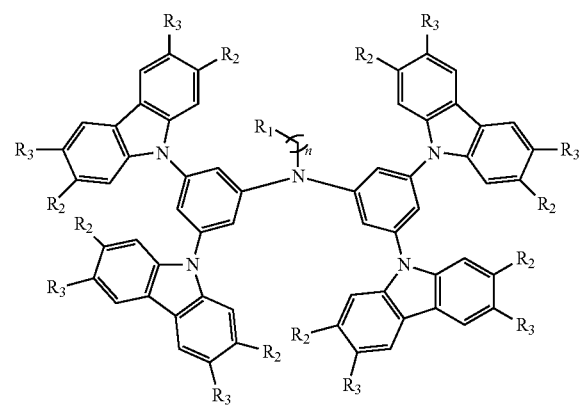

wherein n is 0~8;

$R_2$ and $R_3$ respectively represent H, $CF_3$, CN, $CH_3$ or $C_5H_{11}$; and $R_1$ is one of substituents shown as follows:

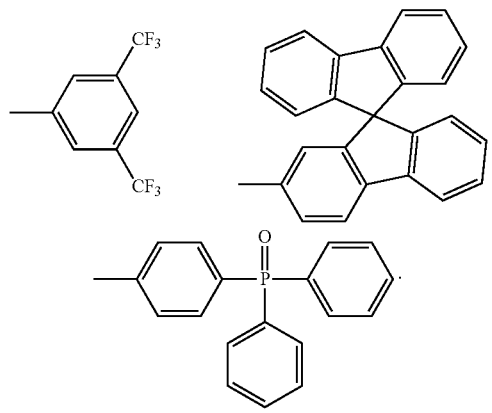

6. The organic electroluminescent apparatus according to claim 5, wherein the host luminescent material comprises the following compound:

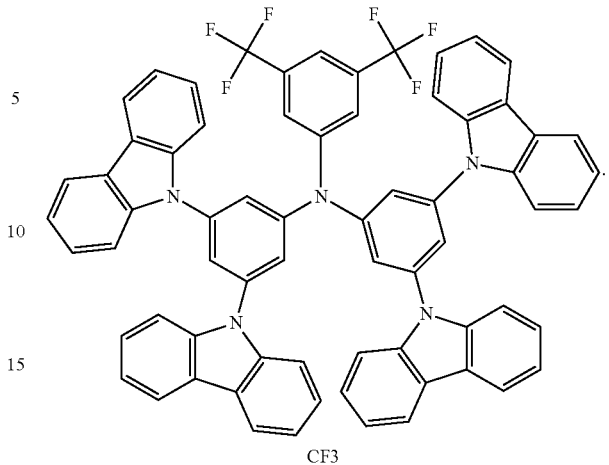

CF3

7. The organic electroluminescent apparatus according to claim 5, wherein the host luminescent material accounts for 80% to 95% by weight of the organic luminescent layer.

8. The organic electroluminescent apparatus according to claim 5, wherein a glass transition temperature (Tg) of the host luminescent material is greater than 80 degrees Celsius.

9. The organic electroluminescent apparatus according to claim 5, wherein the guest luminescent material comprises one of the following compounds:

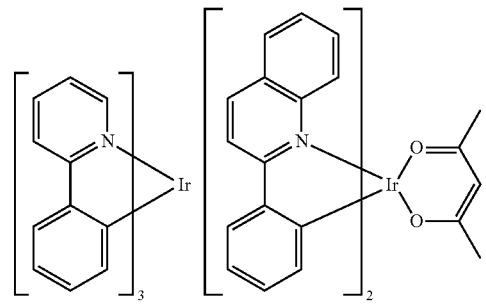

Irppy3  PQIr

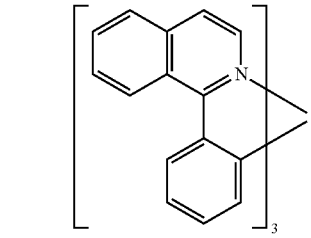

Irpiq

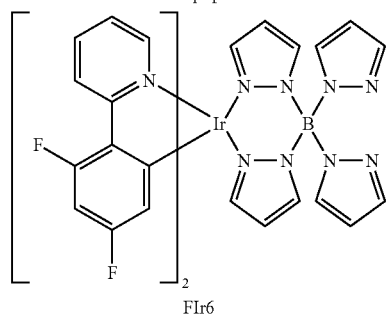

FIr6

-continued

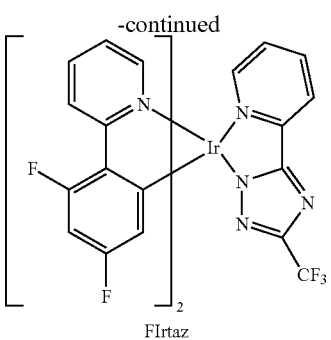

FIrtaz

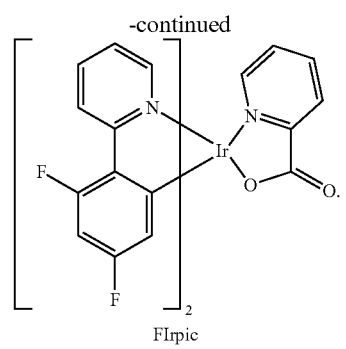

FIrpic

FIrN4

10. The organic electroluminescent apparatus according to claim 5, wherein the guest luminescent material accounts for 5% to 20% by weight of the organic luminescent layer.

11. The organic electroluminescent apparatus according to claim 5, wherein at least one of the first electrode layer and the second electrode layer is of a transparent electrode material.

12. The organic electroluminescent apparatus according to claim 5, further comprising:
   an electron transport layer, located between the organic luminescent layer and the first electrode layer; and
   a hole transport layer, located between the organic luminescent layer and the second electrode layer.

* * * * *